US 12,035,908 B2
Jul. 16, 2024

(12) United States Patent
Lee et al.

(10) Patent No.: US 12,035,908 B2
(45) Date of Patent: Jul. 16, 2024

(54) LAPAROSCOPIC STAPLER

(71) Applicant: ROOTLOC CO., LTD., Seoul (KR)

(72) Inventors: Yoo Min Lee, Seoul (KR); Won Chul Lee, Seoul (KR); Yoo Heun Lee, Seoul (KR); Soon Seok Seo, Daegu (KR)

(73) Assignee: ROOTLOC CO., LTD., Seoul (KR)

( * ) Notice: Subject to any disclaimer, the term of this patent is extended or adjusted under 35 U.S.C. 154(b) by 49 days.

(21) Appl. No.: 17/936,612

(22) Filed: Sep. 29, 2022

(65) Prior Publication Data

US 2023/0013368 A1   Jan. 19, 2023

Related U.S. Application Data

(63) Continuation of application No. PCT/KR2021/003964, filed on Mar. 31, 2021.

(30) Foreign Application Priority Data

Apr. 8, 2020   (KR) .................. 10-2020-0042760

(51) Int. Cl.
| | | |
|---|---|---|
| *A61B 17/068* | (2006.01) | |
| *A61B 17/00* | (2006.01) | |
| *A61B 17/072* | (2006.01) | |
| *B65C 7/00* | (2006.01) | |
| *B25C 7/00* | (2006.01) | |

(52) U.S. Cl.
CPC ...... *A61B 17/068* (2013.01); *A61B 17/00234* (2013.01); *A61B 17/07207* (2013.01); *B65C 7/005* (2013.01); *A61B 2017/00398* (2013.01); *A61B 2017/0042* (2013.01);
(Continued)

(58) Field of Classification Search
CPC . A61B 17/068; A61B 17/0682; A61B 17/072; A61B 17/07207; A61B 17/00234; A61B 2017/07214; A61B 2017/00398; B65C 7/005; B65C 7/008
USPC .......... 227/19, 67, 175.1, 176.1; 606/1, 139, 606/143, 219
See application file for complete search history.

(56) References Cited

U.S. PATENT DOCUMENTS

| | | | | |
|---|---|---|---|---|
| 3,735,908 A | * | 5/1973 | Kinney | ................... B65C 7/008 227/124 |
| 5,738,265 A | * | 4/1998 | Hirai | ...................... B65C 7/005 227/18 |

(Continued)

FOREIGN PATENT DOCUMENTS

| | | |
|---|---|---|
| JP | 2001-354218 A | 12/2001 |
| JP | 2008-188425 A | 8/2008 |

(Continued)

OTHER PUBLICATIONS

International Search Report issued in PCT/KR2021/003964; mailed Jul. 12, 2021.

*Primary Examiner* — Scott A Smith
(74) *Attorney, Agent, or Firm* — Studebaker & Brackett PC

(57) ABSTRACT

The present invention relates to a laparoscopic stapler for suturing body tissue cut during laparoscopic surgery, and more particularly, to a laparoscopic stapler in which implant binding pins to be continuously fired can be correctly positioned using an implant alignment unit for aligning an implant assembly, and an implant assembly pressing member. Therefore, malfunctioning is prevented, and implant loading, transport, and discharge can proceed smoothly.

11 Claims, 7 Drawing Sheets

(52) U.S. Cl.
CPC ... *A61B 17/072* (2013.01); *A61B 2017/07214* (2013.01); *B25C 7/00* (2013.01)

(56) References Cited

U.S. PATENT DOCUMENTS

| | | | | |
|---|---|---|---|---|
| 6,267,285 | B1* | 7/2001 | Raymond | B65C 7/005 |
| | | | | 227/67 |
| 6,564,984 | B1* | 5/2003 | Ueno | B65C 7/005 |
| | | | | 227/18 |
| 8,360,294 | B2* | 1/2013 | Scirica | A61B 17/068 |
| | | | | 227/176.1 |
| 10,524,794 | B2* | 1/2020 | Bolduc | A61B 17/068 |
| 10,561,415 | B2* | 2/2020 | Scirica | A61B 17/068 |
| 2007/0073389 | A1* | 3/2007 | Bolduc | A61F 2/07 |
| | | | | 623/1.36 |
| 2008/0033456 | A1* | 2/2008 | Catanese | A61F 2/0022 |
| | | | | 606/139 |
| 2008/0086154 | A1* | 4/2008 | Taylor | A61B 17/068 |
| | | | | 606/151 |
| 2010/0292712 | A1* | 11/2010 | Nering | A61B 17/0682 |
| | | | | 606/143 |
| 2012/0022557 | A1* | 1/2012 | Cabiri | A61B 17/064 |
| | | | | 606/139 |
| 2013/0197591 | A1* | 8/2013 | Corradi | A61B 17/864 |
| | | | | 606/308 |

FOREIGN PATENT DOCUMENTS

| | | |
|---|---|---|
| JP | 2016-540619 A | 12/2016 |
| KR | 20-021986 Y1 | 7/1982 |
| KR | 10-1407090 B1 | 6/2014 |
| KR | 10-2018-0099146 A | 9/2018 |

* cited by examiner

LAPAROSCOPIC STAPLER

CROSS-REFERENCE TO RELATED APPLICATIONS

The present application is a continuation of International Patent Application No. PCT/KR2021/003964, filed on Mar. 31, 2021, which is based upon and claims the benefit of priority to Korean Patent Application No. 10-2020-0042760 filed on Apr. 8, 2020. The disclosures of the above-listed applications are hereby incorporated by reference herein in their entirety.

BACKGROUND

The inventive concept relates to a laparoscopic stapler.

In general, when a surgery is performed by using laparoscopy, a trocar penetrates skin and a peritoneum and a camera, a medical instrument, and the like are inserted into an inside of the trocar for the surgery, and a body tissue cut during the surgery is sutured by using a suture yarn and a needle.

However, when the body tissue is sutured through the conventional method, a surgery time becomes longer, and a physical burden of a patient increases due to a long-time anesthesia, and a possibility of a medical accident due to a secondary infection and the like becomes higher as well.

Furthermore, to suture the body tissue during a laparoscopic surgery, an implant binding pin is formed of a bio-absorptive material that is the same material as that of the suture yarn that is absorbed into the body after lapse of a specific time, and thus a removal surgery is not necessary.

Accordingly, it is necessary to develop a laparoscopic suture device that may shorten a consumed surgery time by reducing a suture time and reduce a burden of a patient to conveniently suture tissues during a surgery using laparoscopy.

SUMMARY

A technical object to be achieved by the inventive concept is to provide a laparoscopic stapler that may minimize damage to the body tissue by discharging the implant binding pin only by simply gripping the body tissue and only with a touch operation, and thus conveniently suture the body tissue.

The technical problems that are to be solved by the inventive concept are not limited to the above-mentioned ones, and the other technical problems that have not been mentioned will be clearly understood from the following description by an ordinary person in the art, to which the inventive concept pertains.

To solve the above-mentioned problems, according to an embodiment of the inventive concept, a laparoscopic stapler includes a body that fires an inserted implant toward a target portion by using a lever rule to suture the target portion, a through-passage providing part coupled to a muzzle located at one end of the body, and that provides a through-passage, through which the implant fired from the body is inserted into the target portion, and a rear extension part coupled to an opposite end of the body, and including a rail that supports an operation rod such that the operation rod that gives a firing force to the implant to fire the implant is linearly moved.

Furthermore, the body may include a passage, through which the implant is fired, and a space, in which the operation rod performs linear movement for giving the firing force on a rear side of the implant, and the body may further include a first body part formed long along a lengthwise direction of the body, and a second body part formed in a height direction of the body, and that generates a trigger signal for driving the laparoscopic stapler by allowing a user to grip the second body part.

Furthermore, the first body part may further include an implant assembly insertion passage formed on an upper side of the first body part such that an implant assembly, in which the implant and an implant support that supports the implant are coupled to each other is vertically inserted, a pin housing part that provides a space, in which a through-needle bunch part that feeds the implant to insert the implant into the target portion is vertically moved, an implant assembly aligning part formed adjacent to an area, in which a rear end of the pin housing part and the implant assembly cross each other, and that aligns the implant assembly, and an operation rod pressing member coupled to a portion of the operation rod disposed at a rear end of the through-needle bunch part while extending on a line together with the through-needle bunch part, and that transmits power for the linear movement of the operation rod.

Furthermore, the second body part may further include a firing knob gripped by the user, a backward movement switch formed on one side of the firing knob, and that moves the operation rod backwards in a direction of the rear extension part, a lever, one end of which is connected to the firing knob and an opposite end of which is connected to the operation rod pressing member, and that moves the operation rod pressing member by using a moment of a force according to whether the firing knob is gripped, an electric power supply circuit formed at an opposite side of the second body part, which faces the firing knob, and a forward movement switch formed on an opposite side of the firing knob, and that switches on the electric power supply circuit so as to be operated whether the firing knob is gripped by the user such that the current is supplied to the electric power supply circuit or switch off the electric power supply circuit to interrupt supply of a current thereto.

Furthermore, the first body part may include a forward movement/stop switch that stops forward movement of the operation rod disposed on a rear side of the first body part, and a driving motor located on an upper side of the operation rod and a rear side of the operation rod pressing member, that receives electric power from the electric power supply circuit to move the operation rod forwards or rearwards by using a bearing located on a lower side of the operation rod, and driven by the backward movement switch and the forward movement switch, and the operation rod pressing member may be connected to the lever through a hinge, and is driven by the lever to transmit power to the operation rod.

Furthermore, the laparoscopic stapler may further include the operation rod that gives the firing force to the implant to fire the implant, and the operation rod may further include an implant pusher formed at one end of the operation rod to protrude, and that gives the firing force while contacting the implant to fire the implant, an implant pusher guide coupled to the through-needle bunch part, and that guides the implant pusher to allow the implant pusher to fire the implant, and an operation rod wing part formed at an opposite end of the operation rod, and control the driving motor while contacting the forward movement/stop switch according to driving thereof, Furthermore, the rear extension part may further include a backward movement/stop switch located at one end of the rear extension part, and that stops a driving operation of the driving motor, of moving the operation rod in a direction of the rear extension part, according to contact of the operation rod wing part.

Furthermore, the laparoscopic stapler may further include the through-needle bunch part that provides a path, along which the implant is moved, to insert the implant into the target portion, and the through-needle bunch part may further include a through-needle formed at one end thereof and that passes through the target portion by using the implant, a coupling hole formed on one surface of the through-needle bunch part to guide the linear movement of the operation rod, and at least two through-needle legs formed at a rear end of the through-needle bunch part to be spaced apart from each other.

Furthermore, the operation rod may include an operation rod support inserted into and coupled to the coupling hole, and that is linearly moved along a lengthwise direction of the through-needle bunch part, and implant pusher may be formed to be longer than the implant pusher guide and the operation rod support to further prolong an entire length of the operation rod, and the entire length of the operation rod may be formed to be longer than an entire length of the through-needle bunch part.

Furthermore, the implant assembly aligning part may further include an implant assembly pushing preventing member formed adjacent to one side of the implant assembly introduced from the implant assembly insertion passage, and that prevents the implant assembly from being pushed in, an implant aligner formed on one surface of the implant assembly pushing preventing member, and that moves the implant to a location, at which the implant is loaded in the through-needle bunch part according to upward/downward movement thereof, and an implant support pressing member coupled to the implant aligner and that presses the implant support.

Furthermore, the first body part may further include a loading bar connected to the implant support pressing member through a rolling hinge, and in which a boss formed at one end thereof and the operation rod pressing member are connected to each other such that the loading bar is linearly moved according to the movement of the operation rod pressing member, and a loading bar spring loaded at a front end of the loading bar to return the loading bar to an original location, and that gives an elastic force to the loading bar, and the implant aligner may be moved upwards and downwards according to linear movement of the loading bar to load the implant in the through-needle bunch part.

Furthermore, the second body part may further include an implant support keeping part formed on a line together with the implant assembly insertion passage, and that keeps the implant support that is separated from the implant as the implant is fired.

Furthermore, an area of an inlet at one end of the pin housing part may be different from an area of an outlet at an opposite end of the pin housing part, an area at one end of the pin housing part, at which the implant is inserted from the implant assembly aligning part is formed to be larger than an area of an outlet at an opposite end of the pin housing part connected to the through-passage providing part, and a shape of the implant having elasticity may at least partially vary due to a shape of the pin housing part while the implant passes through the pin housing part.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
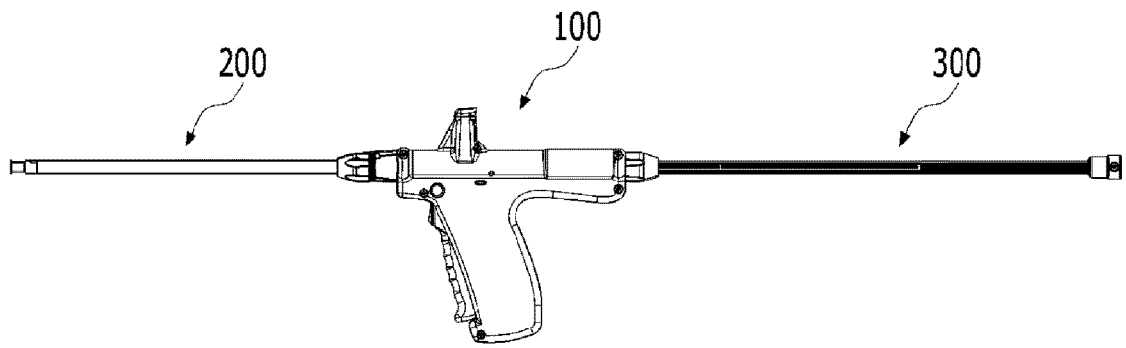
FIG. 1 is a view schematically illustrating a laparoscopic stapler according to an embodiment of the inventive concept.

Hereinafter, the inventive concept will be described with reference to the accompanying drawings. However, the inventive concept may be implemented in various different forms, and is not limited to the embodiments. Further, to clearly describe the inventive concept, parts that are irrelevant to the description are excluded from the drawings and the similar parts are denoted by similar reference numerals throughout the specification.

Throughout the specification, when it is described that a component is "connected (electrically connected, contact, coupled)" to another component, it means not only that they are 'directly connected' to each other but also that they 'are indirectly connected to each other while another component is interposed therebetween'. Further, when it is described that a part includes an element, it may mean that the part may further include a second element without excluding the second element unless a specially contradictory description is made.

The terminologies used herein are provided only to describe specific embodiments, and are not intended to limit the inventive concept. The terms of a singular form may include plural forms unless otherwise specified. The terms "including" and "having" are used to designate that the features, the numbers, the steps, the operations, the elements, the parts, or combination thereof described in the specification are present, and may be understood that one or more other features, numbers, step, operations, elements, parts, or combinations thereof may be added.

Hereinafter, an embodiment of the inventive concept will be described in detail with reference to the accompanying drawings. FIG. 1 is a view schematically illustrating a laparoscopic stapler according to an embodiment of the inventive concept. A laparoscopic stapler according to an embodiment of the inventive concept is a laparoscopic device for suturing a body tissue that is cut during a laparoscopic surgery, and a suture may be performed by using a laparoscopic stapler.

Referring to FIG. 1, a laparoscopic stapler according to an embodiment may include a body 100, a through-passage providing part 200, and a rear extension part 300.

The body 100 may fire the implant that is a suture material for suturing a body tissue during a laparoscopic surgery toward a sutured portion through processes, such as pistol loading, feeding, and separation, by using the lever rule. Here, the target portion may refer to a tissue portion in the body, and in more detail, may refer to a body tissue in a partial area under a peritoneum.

The through-passage providing part 200 may be coupled to the muzzle located at a front end of the body 100, and may provide a through-passage, through which the implant fired from the body is inserted into the target portion.

The rear extension part 300 may include a rail that is formed to be coupled to a rear end of the body 100 and supports the operation rod that gives a firing force to the implant to fire the implant such that the operation rod is linearly moved.

Figure 2:
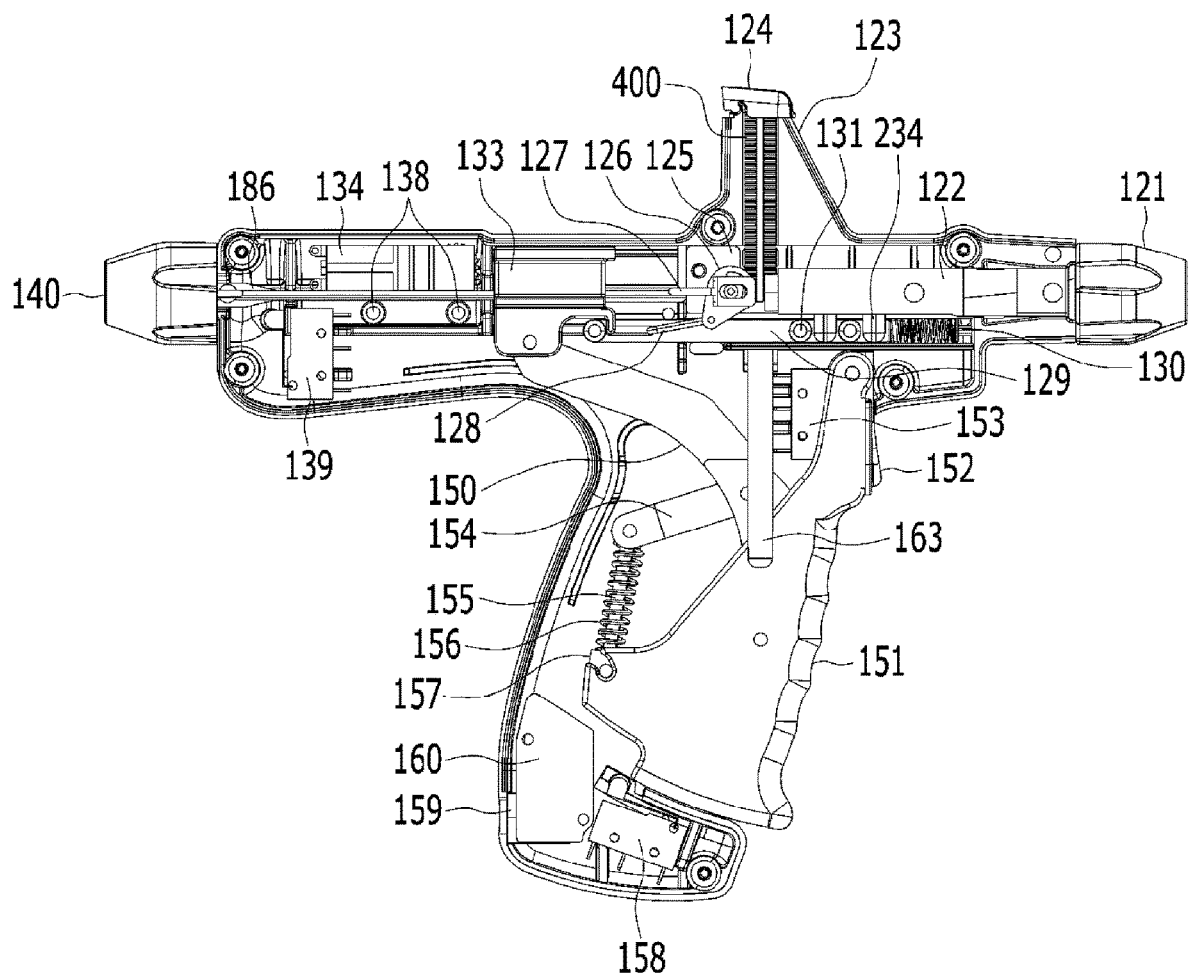
FIG. 2 is a view illustrating an internal configuration of a body part, viewed from a first side, according to an embodiment of the inventive concept.
Figure 3:
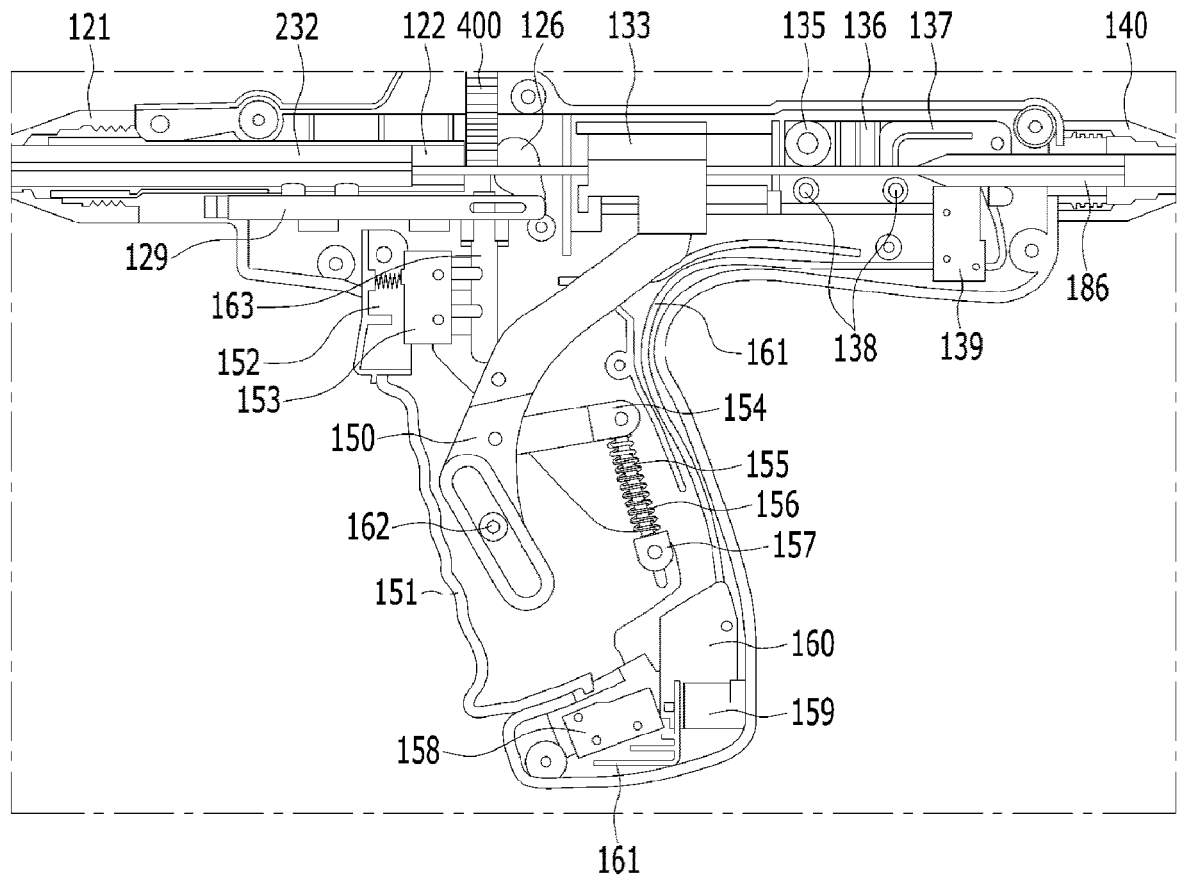
FIG. 3 is a view illustrating an internal configuration of a body part, viewed from a second side, according to an embodiment of the inventive concept.

FIGS. 2 and 3 are views illustrating a configuration of the body part according to an embodiment of the inventive concept in more detail. FIG. 2 is a view illustrating an internal configuration of the body part, viewed from a first side, according to an embodiment of the inventive concept, and FIG. 3 is a view illustrating an internal configuration of the body part, viewed from a second side, according to an embodiment of the inventive concept.

Referring to FIG. 2 first, the configuration of the body part 100 according to the embodiment will be described. Although the body part 100 according to the embodiment is not divided separately in the illustrations of the drawings, it may include a first body part corresponding to a horizontal body part and a second body part corresponding to a vertical body part in a large division.

The first body part may include a passage, through which an implant assembly 400 is fired, and a space, in which an operation rod 180 may perform a linear movement for giving the firing force to a rear side of the implant, and the first body part may be a part that is formed long in a lengthwise direction of the body 100.

The second body part is a part that is formed in a height direction of the body 100, and the second body part may be gripped by the user to generate a trigger signal for driving the laparoscopic stapler.

First, a configuration of the first body part will be described. The first body part according to the embodiment may include a pin housing locking nut 121, a pin housing part 122, an implant assembly insertion passage 123, implant assembly aligning parts 125, 126, and 127, a rolling hinge 128, a loading bar 129, an operation rod pressing member 133, a driving motor 134, a forward movement/stop switch 139, and a rear extension part locking nut 140.

The pin housing locking nut 121 may be formed at a muzzle portion located at the foremost side of the first body part. The pin housing locking nut 121 may fixedly support the pin housing part 122 inserted into the first body part to a rear side surface of the pin housing locking nut 121.

The pin housing part 122 is adapted to provide a space, in which a through-needle bunch part 230 that feeds the implant to the target portion to insert the implant assembly 400 into the target portion may be vertically moved. The pin housing part 122 according to the embodiment is a configuration connected to the through-passage providing part 200, and the through-needle bunch part 230 may be linearly moved in a range of a length of the through-passage providing part 200 from the pin housing part 122. A more detailed description related to this will be described below with reference to FIG. 10.

The implant assembly insertion passage 123, as illustrated in FIG. 2, may be formed on an upper side of the first body part, and may form a passage such that the implant assembly 400 may be vertically inserted.

Figure 4:
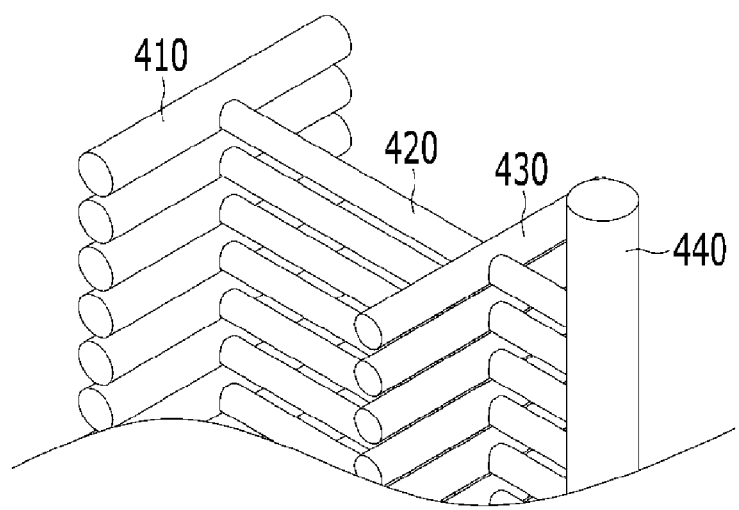
FIG. 4 is a view illustrating a structure of an implant assembly according to an embodiment of the inventive concept.

FIG. 4 is a view illustrating a structure of the implant assembly according to an embodiment of the inventive concept.

Referring to FIG. 4, the implant assembly 400 according to the embodiment may be formed such that implants 410, 420, and 430 are coupled to an implant support 440. In more detail, the implant according to the embodiment may include the implant binding pin one side-shaft 410, the implant binding pin intermediate-shaft 420, and the implant binding pin opposite side-shaft 430. According to an embodiment, the laparoscopic stapler of the inventive concept may include the implant assembly 400 as in FIG. 4, and in another embodiment, may include the implant assembly 400 as an external element.

The implant assembly 400 according to the embodiment may be implemented by an absorptive material or a non-absorptive material, a bio-absorptive material may be used as the absorptive material, and laparoscopic polyethylene (PE) may be used in the case of the non-absorptive material.

Referring to FIG. 2 again, the implant assembly aligning part according to the embodiment may be formed adjacent to an area, in which a rear end of the pin housing part 122 and the implant assembly 400 cross each other, and may align the implant assembly 400. The implant assembly aligning part according to the embodiment may include an implant assembly preventing member 125, an implant aligner 126, and an implant support pressing member 127.

The implant assembly pushing preventing member 125 may be formed adjacent to one side of the implant assembly 400 introduced from the implant assembly insertion passage 123, and may prevent the implant assembly 400 from being pushed in. That is, in order to insert the implant into the target portion, a plurality of implants have to be loaded in the through-needle bunch part 230 sequentially one by one in the implant assembly 400, in which the implants are coupled to each other, and because the implant assembly 400 that is vertically inserted into the implant assembly insertion passage 123 of the inventive concept may be pushed in downwards (in a direction, in which the pin housing part 122 is located), the implant assembly pushing preventing member 125 of the inventive concept may prevent the phenomenon through the alignment.

The implant aligner 126 may be formed on one surface of the implant assembly preventing member 125, and may move the implant to a location for loading the implant in the through-needle bunch part 230 as it is moved upwards and downwards. For example, the implant aligner 126 may lower the implants 410, 420, and 430 one by one from the implant assembly 400, and may make a preparation for loading the lowered implants in the through-needle bunch part 230.

In more detail, the implant assembly aligning part may secure a location, at which the laid "H"-shaped implants 410 to 430 are inserted, at an end of the through-needle bunch part 230.

The implant support pressing member 127 may be coupled to the implant aligner 127, and may press the implant support.

The loading bar 129 may be connected to the implant support pressing member 127 through the rolling hinge 128, and a loading bar leg 132 having a boss shape and the operation rod pressing member 133 may be connected to one end of the loading bar 129 and may be linearly moved according to movement of the operation rod pressing member 133.

Furthermore, an opposite end of the loading bar 129 may be coupled to a loading bar spring 130 disposed on a front side. The loading bar spring 130 according to the embodiment may be located at a front end of the loading bar 129 to return the loading bar 129 to an original location, and may give an elastic force to the loading bar 129.

The operation rod pressing member 133 may be coupled to a portion of the operation rod 180 disposed at a rear end of the through-needle bunch part 230 while extending on a line together with the through-needle bunch part 230, and may transmit power for the linear movement of the operation rod 180.

Figure 5:
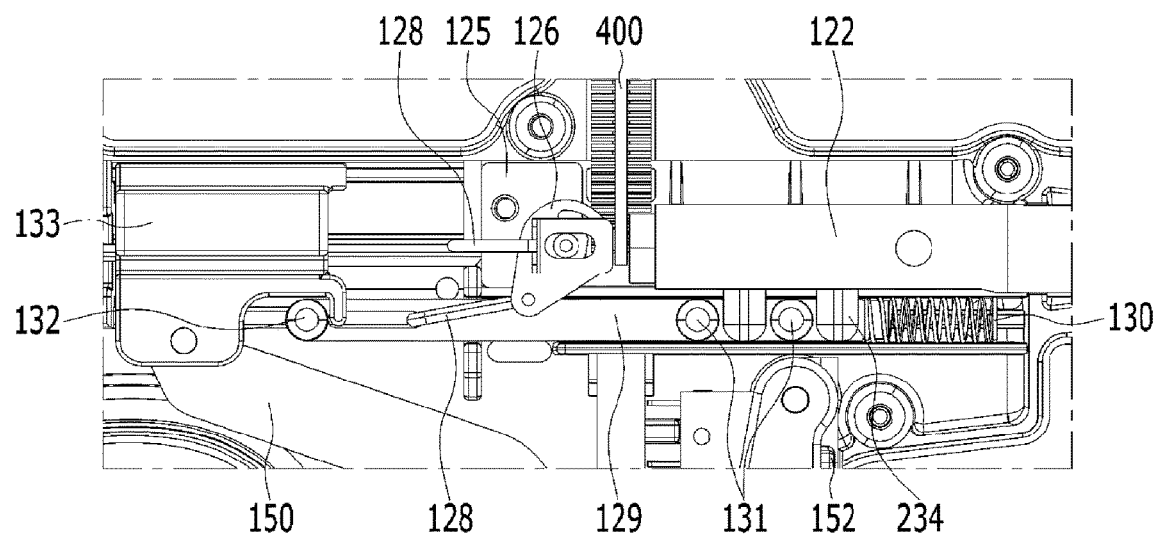
FIG. 5 is an enlarged view illustrating an implant assembly aligning part to describe an operation of the implant assembly aligning part in more detail according to an embodiment of the inventive concept.

FIG. 5 is an enlarged view illustrating the implant assembly aligning part to describe an operation of the implant assembly aligning part in more detail according to an embodiment of the inventive concept. Referring to FIG. 5, the implant assembly aligning part will be described in more detail.

The implant may be loaded in the through-needle bunch part 230, and to feed the implant to an implant pusher 182 of the operation rod 180 and insert the implant into a body tissue, may load another implant located in the implant assembly 400 to the through-needle bunch part 230 again after the implant is separated out of the laparoscopic stapler.

That is, when the implant pusher 182 pushes the implants 410, 420, and 430 stuck to the implant support 440, the implants stuck to the implant assembly 400 are separated one by one, and one separated implant is lowered to be loaded in the through-needle bunch part 230.

Then, an implant assembly aligning part spring may function to help the implant aligner 126 to be easily positioned between the implant binding pin opposite side-shaft 430 and the implant.

Furthermore, the rolling hinge 128 may adhere and fix the implant support 440 such that the implant assembly aligning part spring cannot move the implant support 440 with a force of the spring while the implant support 440 is pressed.

As the rolling hinge 128 is moved backwards in a direction, in which the operation rod pressing member 133 is located, while the implant assembly aligning part spring is compressed when the implant aligner 126 lowers the implant support 440, the implant may be easily lowered, and the implant support 440 may be firmly fixed as the implant support 440 is pushed again by the implant assembly aligning part spring.

Referring back to FIG. 2, the driving motor 134 may be located on an upper side of the operation rod 180 and a rear side of the operation rod pressing member 133, may receive electric power from an electric power supply circuit 160 to be driven, and may control driving through switches 139, 153, 158, and 362. According to the driving of the driving motor 134, the operation rod 180 may be moved forwards in a direction, in which the pin housing part 122 is located, and the operation rod 180 may push the implant to the through-needle bunch part 230.

The driving motor 134 according to the embodiment, as illustrated in FIG. 3, may include a motor gear 135, a motor reduction gear 136, a motor cover 137, and a bearing 138. The motor gear 135 may drive the operation rod 180 such that the operation rod 180 may be moved forwards or rearwards by using the bearing 138.

Furthermore, the motor reduction gear 136 may adjust an rpm (revolutions per minute) to decrease a forward or rearward speed of the operation rod 180. A reduction ratio of the motor reduction gear 136 according to the embodiment may be determined according to an arrangement design of the reduction gear. According to an embodiment, one bearing 138 of the inventive concept may be provided to be implemented to drive the operation rod 180, but two or more bearings 138 may be provided to be implemented to drive the operation rod 180.

According to an embodiment, the forward movement/stop switch 139 may be located on a lower side of the driving motor 134, and may perform a switching operation to stop the forward movement of the operation rod 180.

Furthermore, the rear extension part locking nut 140 may be formed at a rearmost end of the first body part according to the embodiment. The rear extension part locking nut 140 may function to support coupling with the rear extension part 300.

Next, a detailed description of a configuration of the second body part will be described below.

The second body part according to the embodiment may include a lever 150, a firing knob 151, a backward movement switch cover 152, a backward movement switch 153, an operation lever link 154, an operation return bar 155, an operation return spring 156, an operation return bar support 157, a forward movement switch 158, a power supply 159, the electric power supply circuit 160, an electric wire 161, a connector 162, and an implant support keeping part 163.

One end of the lever 150 may be connected to the firing knob 151 and an opposite end thereof may be connected to the operation rod pressing member 133 whereby the operation rod pressing member 133 may be moved by using a moment of a force according to whether a user grips the firing knob 151.

The lever 150, as illustrated in FIG. 3, may be coupled to the firing knob 151 through the connector 162, and a slot may be formed at a point, at which the lever 150 is connected to the firing knob 151. The shape and structure of the lever 150 are not limited to the above-described drawings, and shapes and structures that are widely known in the field of a known tag gun may be applied. Accordingly, the operation rod pressing member 133, as illustrated, may be connected to an upper portion of the lever 150 in a hinge scheme, and thus may be moved forwards and backwards according to driving of the lever 150.

The firing knob 151 is a configuration formed on one side surface of the second body part, and is a part that is gripped by a hand such that the user uses the laparoscopic stapler of the inventive concept.

When the firing knob 151 is pulled inwards as the user grips the firing knob 151, the operation rod pressing member 133 connected to the lever 150 through a hinge is moved while the lever 150 connected to the firing knob 151 is moved.

The backward movement switch cover 152 may be formed on one surface on one side of the firing knob 151, and the backward movement switch 153 may be formed on one side of the firing knob 151 in a direction that is opposite to the backward movement switch cover 153. The backward movement switch cover 152 is formed on the surface to be exposed to an outside of the laparoscopic stapler and the backward movement switch 153 is provided in an interior space of the laparoscopic stapler, and when the operation rod 180 is to return to the original location after the user sutures the target portion, the backward movement switch 153 connected to the backward movement switch cover 152 performs the switching operation as the backward movement switch cover 152 is touched, whereby the driving motor 134 moves the operation rod 180 backwards in a direction of the rear extension part 300.

When the user grips the firing knob 151, the operation return bar 155 that connects the operation lever link 154 and the firing knob 151 is moved together by the operation lever link 154 and the operation return bar support 157, and then, the operation return bar spring 156 formed to surround the operation return bar 155 has a repulsive force as it is compressed. Accordingly, the firing knob 151 gripped by the user is released, the configurations that have been moved as the user grips the firing knob 151 returns to the original state again by the operation return bar spring 156 having the repulsive force.

The forward movement switch 158 may be formed at a lower portion of the firing knob 151, and may switch on the electric power supply circuit 160 or switch off to interrupt supply of the current to the electric power supply circuit 160 as it is operated according to whether the user grips the firing knob. That is, the forward movement switch 158 located below the firing knob 151 is switched on as the user touches (grips) the firing knob 151, and the operation rod 180 connected to the operation rod pressing member 133 is moved toward the through-needle bunch part 230 while the driving motor 134 connected to the forward movement switch 158 is rotated in a forward direction.

The power supply 159 may be formed on an opposite surface of the second body part in a direction that is opposite to the firing knob 151 to supply electric power to the driving motor 134, and may receive electric power (DC) from an outside, and the power supply 159 according to an embodiment of the inventive concept may be implemented by a concentric plug.

The electric power supply circuit 160 may be connected to the power supply 159, and may control driving of the driving motor 134 connected thereto by the electric wire 161 by using the electric power received from the power supply 159.

For example, the electric wire 161, as illustrated in FIG. 3, may be disposed along a rear inner wall of the laparoscopic stapler to connect the electric power supply circuit 160 and the driving motor 134.

The implant support keeping part 163 may be formed on a line together with the implant insertion passage 123, and may keep the implant support 440 that is separated from the implants 410 to 430 to descend as the implants 410 to 430 are fired.

Figure 6:
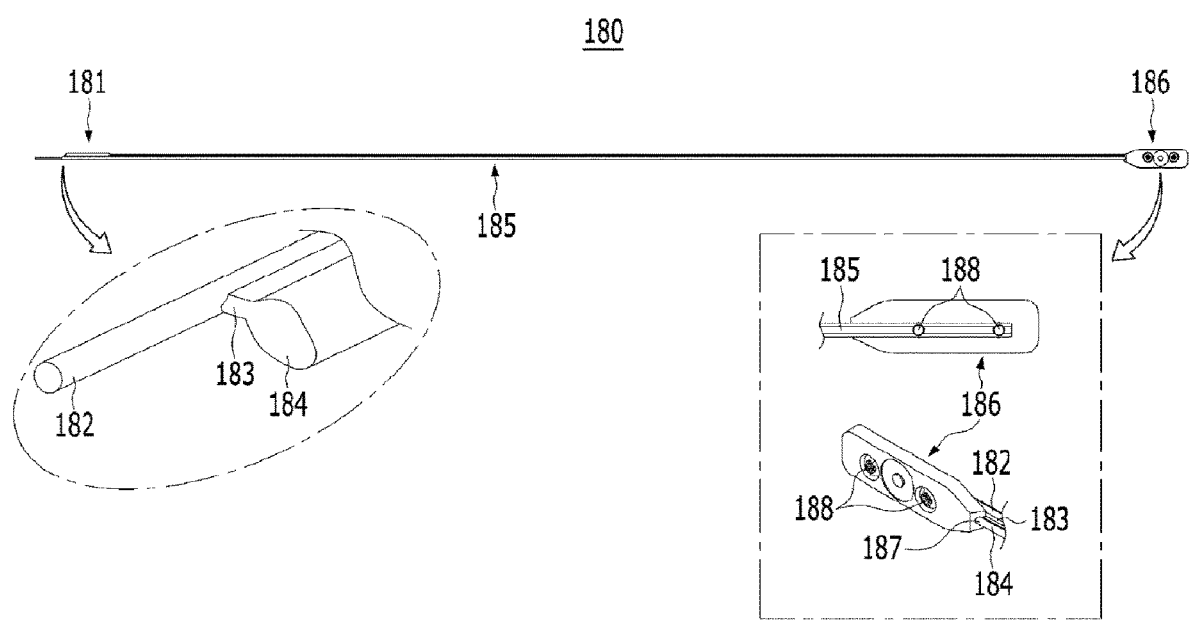
FIG. 6 is a view illustrating an operation rod according to an embodiment of the inventive concept.
Figure 7:
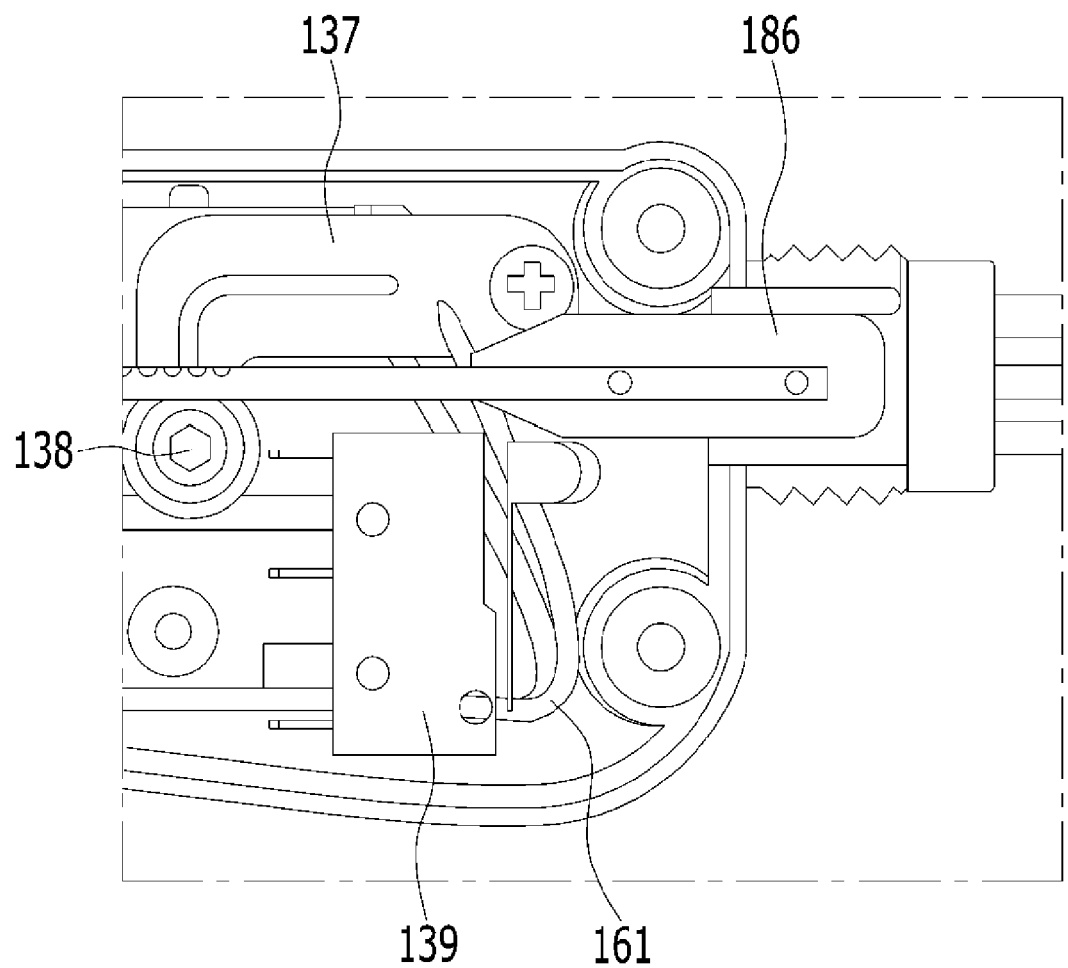
FIG. 7 is a view schematically illustrating an operation rod wing part according to an embodiment of the inventive concept.

FIGS. 6 and 7 are views illustrating the operation rod according to an embodiment of the inventive concept.

The operation rod 180 according to an embodiment of the inventive concept, as illustrated in FIG. 6, may be implemented to have a shape that is long and thin in a lengthwise direction thereof, and may include one end part 181 for feeding the implant, an opposite end part having an operation rod wing part 186, and an operation rod gear 185 driven by the motor gear 135.

In the one end part 181 of the operation rod 180, the implant pusher 182, an implant pusher guide 183, and an operation rod support 184 may be connected to each other.

The implant pusher 182 may be formed in the one end part 181 of the operation rod to protrude, and may give a firing force while contacting the implants 410, 420, and 430 to fire the implants to the through-needle bunch part 230.

The implant pusher guide 183 may be coupled to the through-needle bunch part 230, and may guide the implant pusher 182 to allow the implant pusher 182 to fire the implants 410 to 430.

The operation rod support 184 may be inserted into and coupled to a coupling hole 232 formed in the through-needle bunch part 230, and may feed the implants by using the implant pusher 182 along the coupling hole 232 of the through-needle bunch part 230.

According to a more detailed embodiment, as the implant pusher 182 is moved along the coupling hole 232 formed on one side of the through-needle bunch part, the implants 410 to 430 loaded in the through-needle bunch part 230 may be fed to the through-passage providing part 200 by the implant assembly aligning part. Because the implant pusher guide 183 according to the embodiment is moved along the coupling hole 232, a total length of the laparoscopic stapler of the inventive concept may be reduced.

The operation rod wing part 186 may be formed at an end of the operation rod 180, and may contact the backward movement/stop switch 362 disposed on a rear side of the rear extension part 300 to stop backward driving of the driving motor 134 when the operation rod 180 is moved rearwards.

The operation rod wing part 186 according to the embodiment may have a hole 187 that is to be coupled to the operation rod gear 185 at one end thereof, a part 184 that extends from the implant support may be inserted into the hole 187, and the operation rod gear 185 and a bolt 188 may be coupled to each other. According to an embodiment, the operation rod wing part 186 may be implemented by an area that is larger than that of the operation rod gear 185.

For example, an entire length of the operation rod 180 according to the embodiment from the implant pusher 182 of the one end part 181 to the operation rod wing part 186 may be 470 mm or less, and the length from the piston support 184 of the one end part 181 to the operation rod wing part 186 may be 430 mm or less.

Referring to FIG. 7, it may be identified that as the operation rod wing part 186 is inserted to a point, the operation rod wing part 186 is inserted into the rear extension part locking nut 140 of the body 200.

Figure 8A:
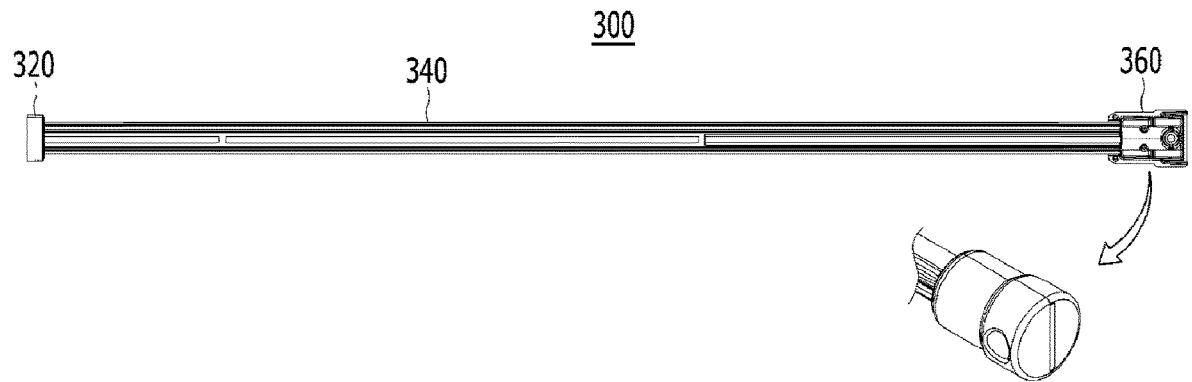
FIGS. 8A to 8C are views schematically illustrating a configuration of a rear extension part according to an embodiment of the inventive concept.
Figure 8B:
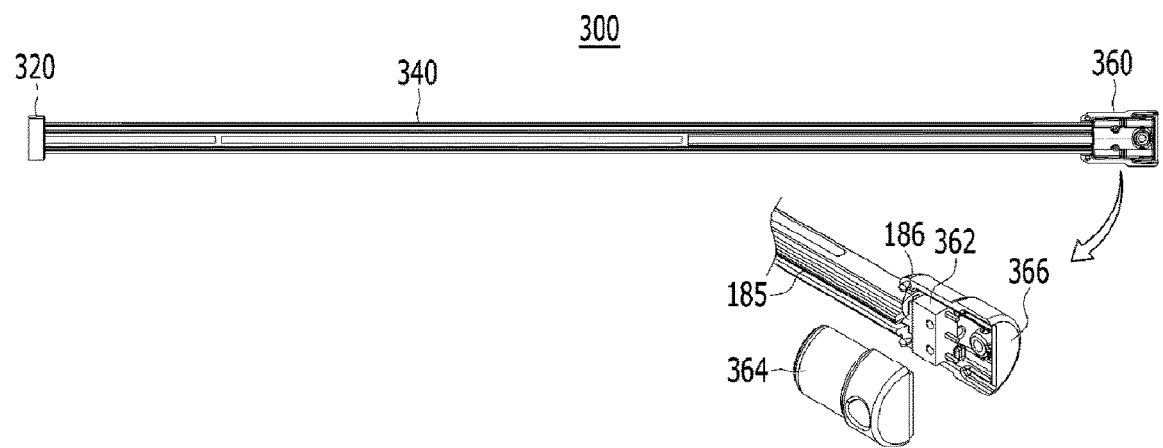
Figure 8C:
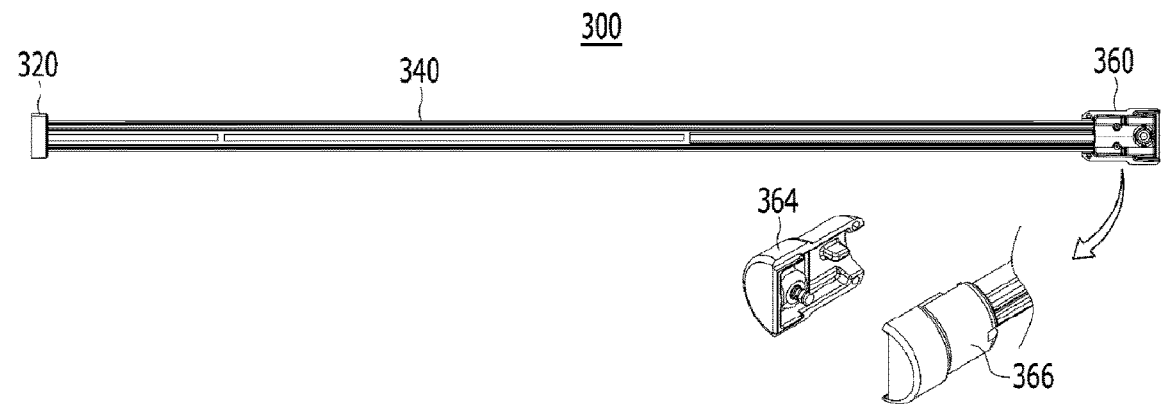

FIGS. 8A to 8C are views schematically illustrating a configuration of the rear extension part according to an embodiment of the inventive concept.

The rear extension part 300 according to the embodiment may include one end 320 connected to the rear extension part locking nut 140, a rear extension passage 340 that provides a space, in which the operation rod 180 is linearly moved, and an opposite end 360 of the rear extension part 300, at which the backward movement/stop switch 362 is located.

FIGS. 8A to 8C are enlarged views of the opposite end 360 of the rear extension part 300. As illustrated in FIGS. 8B and 8C, the opposite end 360 of the rear extension part may include a first case 366 that is connected to the rear extension passage 340 and defines a space, in which the backward movement/stop switch 362 is to be provided, and a second case 364 that covers the backward movement/stop switch 362 as it is separated from or coupled to the first case 366.

The backward movement/stop switch 362 may be disposed between the first case 366 and the second case 364, and may control backward driving of the driving motor 134 as it performs a switching operation by a touch of the operation rod wing part 186 that is moved backwards.

Although not illustrated in FIGS. 8A to 8C, in the rear extension part according to an embodiment, a rail that supports the operation rod wing part 186 may be provided along the rear extension passage 340 such that the operation rod wing part 186 may be easily moved. Furthermore, the backward movement/stop switch 362 may be disposed at an end of the rail.

Figure 9:
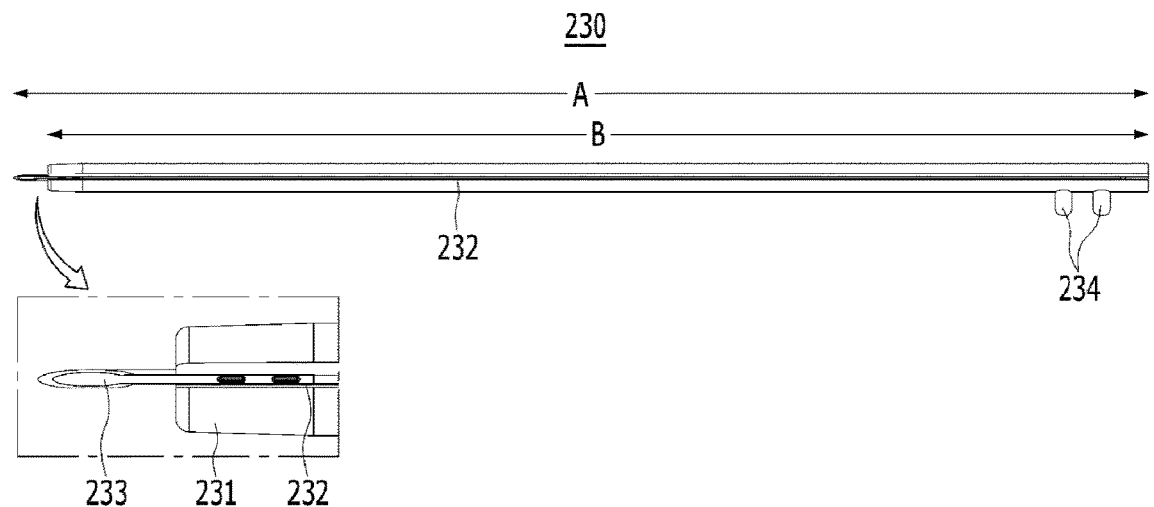
FIG. 9 is a view illustrating a through-needle bunch part according to an embodiment of the inventive concept.

FIG. 9 is a view illustrating the through-needle bunch part according to an embodiment of the inventive concept.

The through-needle bunch part 230 according to an embodiment of the inventive concept provides a path, along which the implants 410 to 430 may be moved, to insert the implants 410 to 430 into the target portion. Referring to FIG. 9, the through-needle bunch part 230 according to the embodiment may include a through-needle housing 231, the coupling hole 232, a through-needle 233, and a through-needle leg 234.

The through-needle housing 231 according to FIG. 9 that is an embodiment may be implemented to have a cylindrical shape, a portion of the through-needle 233 that is to pass through the target portion may be inserted into an end thereof, and the coupling hole 232, to which the implant pusher 182 of the operation rod 180 and the operation rod gear 185 may be coupled in a lengthwise direction of the through-needle housing 231 may be formed on one side thereof. Furthermore, the through-needle leg 234 may be formed at an opposite end of the through-needle housing 231.

The implant opposite-side shaft 430 may be inserted into the coupling hole 232 located at an opposite end of the through-needle housing 231, and the implants 410 to 430 may be separated after the through-needle 233 passes through the body tissue of the target portion.

In a more detailed embodiment, the operation rod 180 may be coupled to the coupling hole 233 of the through-needle bunch part 230 to move the implant pusher 182 into the through-needle bunch part 230 like a rail, the implant pusher guide 183 may be moved over the coupling hole 233, and the operation rod support 184 may move the implants 410 to 430 forwards in a direction of a protector 220 while pushing the implants 410 to 430 together with the through-needle bunch part 230 in an interior of the pin housing part 122.

As an example, after the implants are separated from and inserted into the tissues that are passed through by the through-needle 233 as the operation rod 180 is moved, the operation rod wing part 186 touches the forward movement/stop switch 139 to stop driving of the driving motor 134 and thus move the operation rod 180 forwards. A user has to grip the firing knob 151 until the operation is finished. That is, the forward movement switch 158 is operated due to a pressure applied to the firing knob 151, and the operation rod wing part 186 touches the forward movement/stop switch 139 that is switched on, whereby the forward movement of the operation rod 180 is stopped as the forward movement/stop switch 139 is switched on.

Thereafter, when the user releases the firing knob 151, the internal configurations moved by the firing knob 151 returns to the original location again, and the driving motor 134 is driven in a backward direction as the backward movement switch 153 is touched when the user presses the backward movement switch cover 152, and thus the operation rod 180 that was moved forwards returns to the original location again.

Then, when the operation rod wing part 186 touches the backward movement/stop switch 362, the driving motor 134 stops the backward driving.

The through-needle leg 234 according to the embodiment may be two through-needle legs that are spaced apart from each other by a specific interval distance.

Referring back to FIG. 5, the through-needle leg 234 may be located while a gap is formed between loading bar legs 131 of the loading bar 129, and as the loading bar 129 is moved by the gap between the through-needle legs 234, the implant assembly aligning part may load the implants 410 to 430 in the through-needle bunch part 230.

When the implants 410 to 430 are loaded at an end of the through-needle bunch part 230, the loading bar leg 131 is directly pushed, and accordingly, the operation rod 180 is moved forwards together with the through-needle bunch part 230 so that the through-needle 233 located at an end of the through-needle bunch part 230 is moved to an end of the through-passage providing part 200 that contacts the target portion, whereby the through-needle 233 passes through the target portion.

A length "A" from the through-needle 233 to an opposite end of the through-needle housing 231 of the through-needle bunch part may be implemented to be 320 mm to 340 mm, and a length "B" from one end of the through-needle housing 231 to an opposite end of the through-needle housing 231 may be implemented to be 310 mm to 330 mm. For example, it is preferable that the length "A" from the through-needle 233 to the opposite end of the through-needle housing 231 may be implemented to be 329.5 mm, and the length "B" to the opposite end of the through-needle housing 231 may be implemented to be 319.5 mm. When an entire length of the laparoscopic stapler according to an embodiment of the inventive concept is to be adjusted according to a design of an ordinary person in the art, a total length to be implemented may be adjusted by adjusting lengths of the through-needle bunch part 230 and the operation rod 180.

Figure 10:
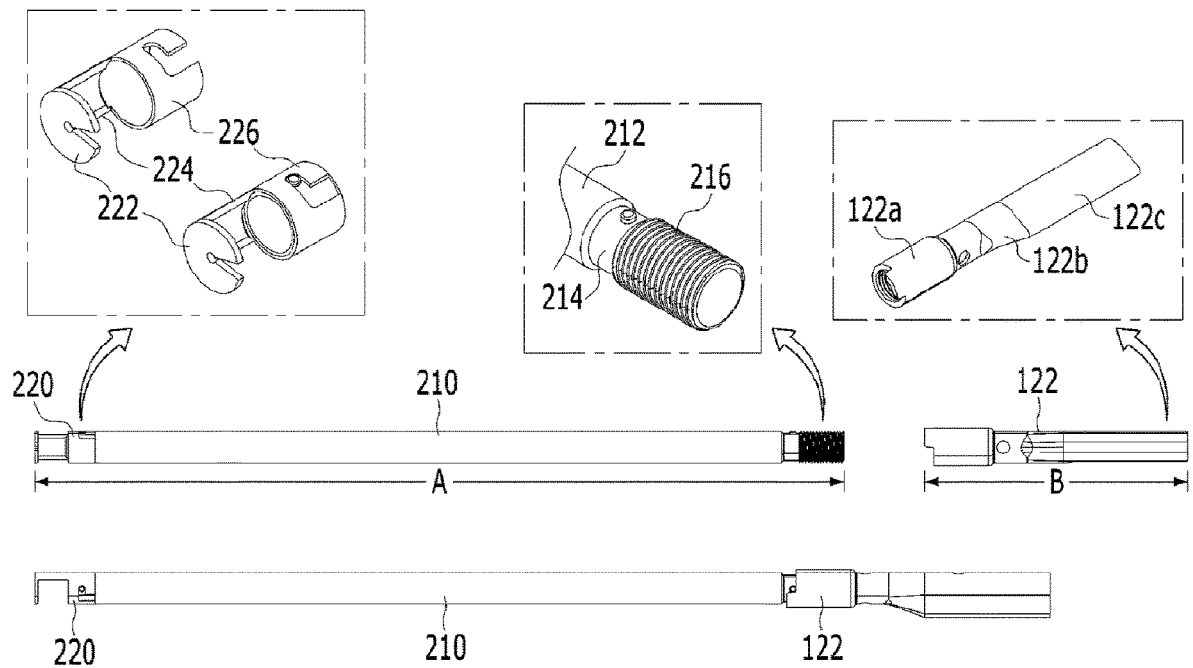
FIG. 10 is a view schematically illustrating a configuration of a through-passage providing part according to an embodiment of the inventive concept.

FIG. 10 is a view schematically illustrating a configuration of the through-passage providing part according to an embodiment of the inventive concept.

Referring to FIG. 10, the through-passage providing part 200 according to the embodiment may include the protector 220 and a through-passage housing 210.

The protector 220 is located at one end of the through-passage providing part 200 that contacts the target portion, and the protector 220 contacts such that a portion of the tissue of the target portion may be inserted into an interior thereof to prevent separation of the tissue when the through-needle 233 passes through the tissue of the target portion, which is to be sutured, whereby the through-needle 233 passes through the tissue of the target portion.

For example, the protector 220, as illustrated in FIG. 10, may include a contact part 222 that directly contacts the target portion and defines a hole, through which the through-needle 233 may pass, in one area, a through-passage housing connector 226 connected to the through-passage housing 210, and an intermediate support part 224 that connects the contact part 222 and the through-passage housing connector 226.

The through-passage housing 210 is a configuration that provides a through-passage, in which the through-needle bunch part 230 may be linearly moved, and the through-passage housing 210 according to an embodiment may be implemented of a steel material.

For example, the through-passage housing 210, as illustrated in FIG. 10, may include a passage 212, and a through-passage connector 216 connected to the pin housing part 122, and may be formed between the passage 212 and the through-passage connector 216 to be implemented to have a diameter that is smaller than a diameter of the passage 212 and a diameter of the through-passage connector 216.

The through-passage connector 216 may be implemented to be coupled to the pin housing part 122 located in the first body part.

According to FIG. 10 that is an embodiment, the pin housing part 122 may include a pin housing connector 122a coupled and connected to the through-passage connector 216, a width of an opposite end 122c of the pin housing part 122 may be larger than that of a pin housing connector 122a, one side of the opposite end is formed to be rounded, and a hole, through which the through-needle leg 234 may be inserted, may be provided between (122b) the opposite end 122c and the pin housing connector 122c. For example, the pin housing part 122 of the inventive concept may be implemented of a plastic material.

The implants 410 to 430 may be deformed from the laid "H" shape to an distorted laid "H" shape by a space inclination that becomes narrower while they pass through reference numeral 122a from reference numeral 122b when they pass through the pin housing part 122.

The implant according to the embodiment may be implemented of an elastic material, and thus a diameter of the pin housing part 122 may be decreased as a shape of the implant is partially deformed while the implant passes through the pin housing part 122, whereby a space, in which the pin housing part 122 is installed, may be minimized.

As an embodiment, the length "A" of the protector 220 from the through-passage housing 210 may be implemented to be 320 mm to 340 mm, and the length "B" of the pin housing part may be implemented to be 330 mm to 350 mm. For example, it is preferable that the length "A" of the protector 220 from the through-passage housing 210 may be implemented to be 11 mm, and the length "B" of the pin housing part may be implemented to be 341 mm to 361 mm.

That is, a total length of the laparoscopic stapler according to an embodiment of the inventive concept may be implemented to be 820 mm to 840 mm.

Figure 11A:
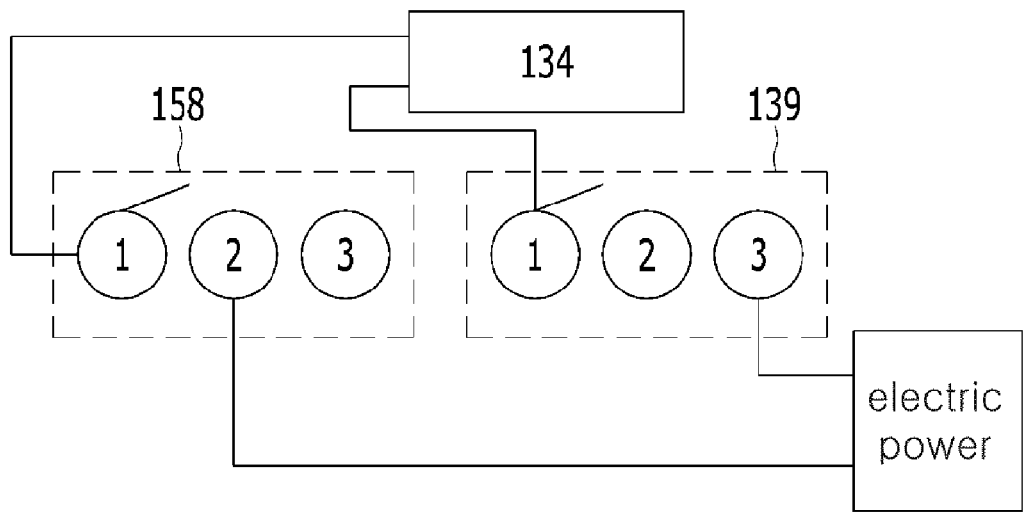
FIGS. 11A and 11B are conceptual views for operations of switches according to an embodiment of the inventive concept.
Figure 11B:
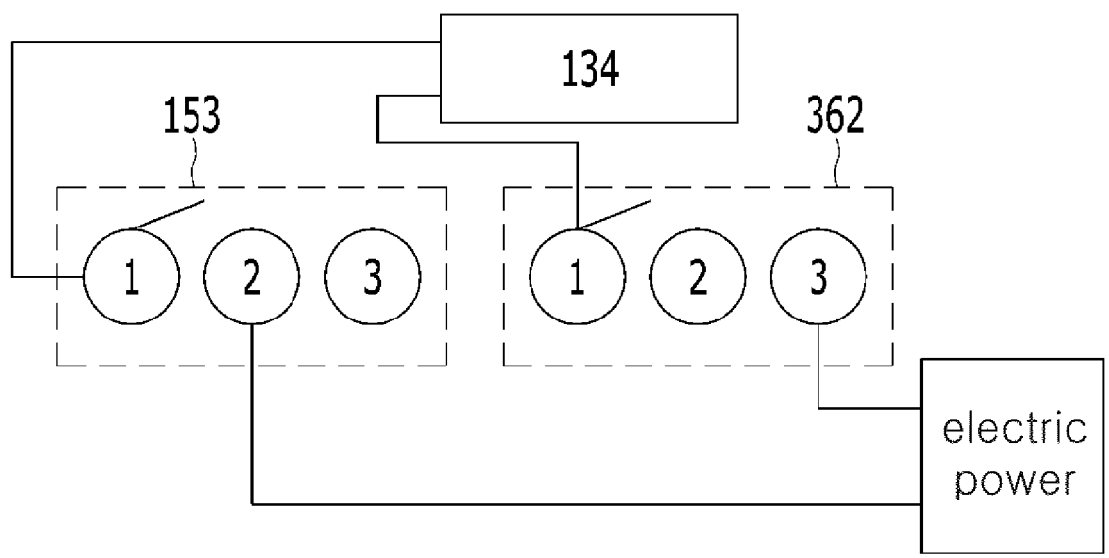

FIGS. 11A and 11B are conceptual views for operations of switches according to an embodiment of the inventive concept.

FIG. 11A is a view illustrating a conceptual view of operations of the forward movement switch 158 and the forward movement/stop switch 139 for controlling forward driving of the driving motor 134. For example, each of the forward movement switch 158 and the forward movement/stop switch 139 may include three terminals 1, 2, and 3. For example, a first terminal 1 of the forward movement switch 158 and a first terminal 1 of the forward movement/stop switch 139 may be implemented as com terminals, a second terminal 2 of the forward movement switch 158 and a third terminal 3 of the forward movement/stop switch 139 may be implemented as nc terminals, and a third terminal 3 of the forward movement switch 158 and a second terminal 2 of the forward movement/stop switch 139 may be implemented as no terminals. Here, a ground terminal may be connected to the third terminal 3 of the forward movement switch 158 and the second terminal 2 of the forward movement/stop switch 139.

Similarly, FIG. 11B is a view illustrating a conceptual view of operations of the backward movement switch 153 and the backward movement/stop switch 362 for controlling backward driving of the driving motor 134. A description of the backward movement switch 153 and the backward movement/stop switch 362 is substantially the same as the above description of the forward movement switch and the forward movement/stop switch, and thus a detailed description thereof will be omitted.

As the firing knob 151 is pressed by the user, the forward movement switch 158 is switched on, and thus when electric power is supplied to the driving motor, the implant is separated to the target portion as the operation rod 180 is moved forwards.

Then, as the operation rod 180 is moved forwards, it touches the forward movement/stop switch 139 that is switched on, and the forward movement/stop switch 139 is switched off due to the touch, and thus the supply of the electric power to the driving motor 134 is interrupted.

Thereafter, when the user releases the firing knob 151, the operation rod pressing member 133, the rolling bar 129, and the through-needle bunch part 230 returns to the original locations again while the firing knob 151 returns to the original location again, and the forward movement switch 158 is switched off.

Then, when the user presses the backward movement switch cover 152 to return the operation rod 180 that has not returned to the original location yet to the original location, the operation rod 180 may be moved backwards to an initial location, and when the operation rod wing part 186 that is moved backwards touches a backward movement/stop switch 326, the driving of the driving motor 134 may be stopped by switching off the backward movement/stop switch 326.

Hereinafter, an operation sequence of the laparoscopic stapler according to an embodiment of the inventive concept will be briefly described below.

First, the user pulls the firing knob 151, the implants 410 to 430 are mounted on the through-needle bunch part 230.

Furthermore, the through-needle 233 of the through-needle bunch part 230 passes through the body tissue of the target portion.

As the power supply 159 supplies electric power, the driving motor 134 is driven, the operation rod 180 is moved forwards in a direction of the through-needle bunch part 230 as the driving motor is driven, and thus the implants 410 to 430 are moved forwards.

Furthermore, when the implants 410 to 430 are separated out of the through-needle 233, the driving motor 134 stops the forward driving.

When the firing knob 151 is released from a hand after the user identifies whether the implant is sutured at the target portion, the configurations that are moved forwards, except for the operation rod 180, return to the original location.

Furthermore, when the user touches the backward movement switch cover 152, the driving motor 134 is driven backwards and the operation rod 180 is driven backwards in a direction of the rear extension part 300, and accordingly, when the operation rod wing part 186 touches the backward movement/stop switch 362 located at an end of the rear extension part 300, the backward driving of the driving motor 134 is stopped and the operation rod 180 is stopped after being moved backwards.

The description of the inventive concept is exemplary, and it can be understood that those skilled in the art to which the inventive concept pertains can easily modify the inventive concept into other detailed forms without changing the technical spirits or the essential features. Therefore, the above-described embodiments are exemplary in all aspects, and should be construed not to be restrictive. For example, the elements described in a single type may be distributed when being carried out, and the elements described as being distributed may be carried out while being coupled to each other.

According to an embodiment of the inventive concept, the laparoscopic stapler may minimize damage to the body tissue by discharging the implant binding pin only by simply gripping the body tissue and only with a touch operation, and thus conveniently suture the body tissue.

Furthermore, according to the embodiment of the inventive concept, the implant binding pins to be continuously fired may be disposed at a proper location by using the implant alignment unit that aligns the implant assembly and the implant assembly pressing member, and thus an operation error may be prevented, and implant loading, transport, and discharge can proceed smoothly.

It should be understood that the effects of the inventive concept are not limited to the above-described ones and includes all effects that may be derived from the construction of the inventive concept claimed in the claims.

The scope of the inventive concept is determined by the claims rather than the description of the inventive concept, and all changes or modifications derived from the meanings and scopes of the claims and the equivalents thereof are construed to be included in the scope of the inventive concept.

The laparoscopic stapler of the inventive concept may minimize damage to the body tissue by discharging the implant binding pin only by simply gripping the body tissue and only with a touch operation, and thus conveniently suture the body tissue.

What is claimed is:

1. A laparoscopic stapler comprising:
   a body configured to fire an inserted implant toward a target portion;
   a through-passage providing part coupled to a front distal end of the body, and comprising a through-passage, wherein the implant fired from the body is configured to move through the through-passage toward the target portion; and
   a rear extension part coupled to a back distal end of the body, and configured to support an operation rod,
   wherein the body comprises:
     a passage, wherein the implant fired from the body is configured to move through the passage toward the through-passage; and
     a space, wherein the operation rod configured to perform linear movement, and
   wherein the body further includes:
     a first body part; and
     a second body part configured to be gripped by a user, and
   wherein the first body part comprises:
     an implant assembly insertion passage formed on an upper side of the first body part such that an implant assembly, in which the implant and an implant support that supports the implant are coupled to each other is vertically inserted;
     a pin housing part configured to provide a space, in which a through-needle bunch part that feeds the implant to insert the implant into the target portion is vertically moved;
     an implant assembly aligning part formed adjacent to an area, in which a rear end of the pin housing part and the implant assembly cross each other, and configured to align the implant assembly; and
     an operation rod pressing member coupled to a portion of the operation rod disposed at a rear end of the through-needle bunch part while extending on a line together with the through-needle bunch part, and configured to transmit power for the linear movement of the operation rod.

2. The laparoscopic stapler of claim 1, wherein the second body part further includes:
   a firing knob gripped by the user;
   a backward movement switch formed on one side of the firing knob, and configured to move the operation rod backwards in a direction of the rear extension part;
   a lever, one end of which is connected to the firing knob and an opposite end of which is connected to the operation rod pressing member, and configured to move the operation rod pressing member by using a moment of a force according to whether the firing knob is gripped;
   an electric power supply circuit formed at an opposite side of the second body part, which faces the firing knob; and
   a forward movement switch formed on an opposite side of the firing knob, and configured to switch on the electric power supply circuit so as to be operated whether the firing knob is gripped by the user such that a current is supplied to the electric power supply circuit or switch off the electric power supply circuit to interrupt supply of the current thereto.

3. The laparoscopic stapler of claim 2, wherein the first body part includes:
   a forward movement/stop switch configured to stop forward movement of the operation rod disposed on a rear side of the first body part; and
   a driving motor located on an upper side of the operation rod and a rear side of the operation rod pressing member, configured to receive electric power from the electric power supply circuit to move the operation rod forwards or rearwards by using a bearing located on a lower side of the operation rod, and driven by the backward movement switch and the forward movement switch,
   wherein the operation rod pressing member is connected to the lever through a hinge, and is driven by the lever to transmit power to the operation rod.

4. The laparoscopic stapler of claim 3, further comprising:
   the operation rod that gives the firing force to the implant to fire the implant,
   wherein the operation rod further includes:
   an implant pusher formed at one end of the operation rod to protrude, and configured to give the firing force while contacting the implant to fire the implant;
   an implant pusher guide coupled to the through-needle bunch part, and configured to guide the implant pusher to allow the implant pusher to fire the implant; and
   an operation rod wing part formed at an opposite end of the operation rod, and control the driving motor while contacting the forward movement/stop switch according to driving thereof.

5. The laparoscopic stapler of claim 4, wherein the rear extension part further includes:
   a backward movement/stop switch located at one end of the rear extension part, and configured to stop a driving operation of the driving motor, of moving the operation rod in a direction of the rear extension part, according to contact of the operation rod wing part.

6. The laparoscopic stapler of claim 4, further comprising:
the through-needle bunch part configured to provide a path, along which the implant is moved, to insert the implant into the target portion,
wherein the through-needle bunch part further includes:
a through-needle formed at one end thereof and configured to pass through the target portion by using the implant;
a coupling hole formed on one surface of the through-needle bunch part to guide the linear movement of the operation rod; and
at least two through-needle legs formed at a rear end of the through-needle bunch part to be spaced apart from each other.

7. The laparoscopic stapler of claim 6, wherein the operation rod includes an operation rod support inserted into and coupled to the coupling hole, and configured to be linearly moved along a lengthwise direction of the through-needle bunch part, and
wherein the implant pusher is formed to be longer than the implant pusher guide and the operation rod support to further prolong an entire length of the operation rod, and the entire length of the operation rod is formed to be longer than an entire length of the through-needle bunch part.

8. The laparoscopic stapler of claim 1, wherein the implant assembly aligning part further includes:
an implant assembly pushing preventing member formed adjacent to one side of the implant assembly introduced from the implant assembly insertion passage, and configured to prevent the implant assembly from being pushed in;
an implant aligner formed on one surface of the implant assembly pushing preventing member, and configured to move the implant to a location, at which the implant is loaded in the through-needle bunch part according to upward/downward movement thereof; and
an implant support pressing member coupled to the implant aligner and configured to press the implant support.

9. The laparoscopic stapler of claim 8, wherein the first body part further includes:
a loading bar connected to the implant support pressing member through a rolling hinge, and in which a boss formed at one end thereof and the operation rod pressing member are connected to each other such that the loading bar is linearly moved according to the movement of the operation rod pressing member; and
a loading bar spring loaded at a front end of the loading bar to return the loading bar to an original location, and configured to give an elastic force to the loading bar, and
wherein the implant aligner is moved upwards and downwards according to linear movement of the loading bar to load the implant in the through-needle bunch part.

10. The laparoscopic stapler of claim 1, wherein the second body part further includes:
an implant support keeping part formed on a line together with the implant assembly insertion passage, and configured to keep the implant support that is separated from the implant as the implant is fired.

11. The laparoscopic stapler of claim 1, wherein an area of an inlet at one end of the pin housing part is different from an area of an outlet at an opposite end of the pin housing part, an area at one end of the pin housing part, at which the implant is inserted from the implant assembly aligning part is formed to be larger than an area of an outlet at an opposite end of the pin housing part connected to the through-passage providing part, and a shape of the implant having elasticity at least partially varies due to a shape of the pin housing part while the implant passes through the pin housing part.

* * * * *